United States Patent
Iwakuma et al.

(10) Patent No.: US 7,250,532 B2
(45) Date of Patent: Jul. 31, 2007

(54) METHOD FOR PRODUCING AROMATIC AMINO COMPOUND

(75) Inventors: Toshihiro Iwakuma, Chiba (JP); Fumio Moriwaki, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 0 days.

(21) Appl. No.: 11/239,116

(22) Filed: Sep. 30, 2005

(65) Prior Publication Data

US 2006/0030736 A1 Feb. 9, 2006

Related U.S. Application Data

(63) Continuation of application No. 10/469,702, filed as application No. PCT/JP02/02132 on Mar. 7, 2002, now abandoned.

(30) Foreign Application Priority Data

Mar. 16, 2001 (JP) .............................. 2001-76302

(51) Int. Cl.
*C07C 211/00* (2006.01)
(52) U.S. Cl. ...................... 564/307; 564/308; 564/463; 564/404
(58) Field of Classification Search ................ 564/463, 564/307, 308, 404
See application file for complete search history.

(56) References Cited

U.S. PATENT DOCUMENTS

| | | | | |
|---|---|---|---|---|
| 5,648,539 | A | * | 7/1997 | Goodbrand ................. 564/309 |
| 5,654,482 | A | * | 8/1997 | Goodbrand ................. 564/405 |
| 5,723,669 | A | * | 3/1998 | Goodbrand et al. ........ 564/307 |
| 5,902,901 | A | * | 5/1999 | Goodbrand et al. ........ 564/405 |
| 5,929,281 | A | | 7/1999 | Nishiyama et al. |
| 6,476,265 | B1 | * | 11/2002 | Spreitzer et al. ............ 564/307 |

FOREIGN PATENT DOCUMENTS

| | | | |
|---|---|---|---|
| JP | 56-123964 | | 9/1981 |
| JP | 63-035548 | | 2/1988 |
| JP | 63035548 | * | 2/1988 |
| JP | 06-100503 | | 4/1994 |
| JP | 06100503 | * | 4/1994 |
| JP | 10310561 | * | 11/1998 |
| WO | WO 99/12888 | | 3/1999 |

OTHER PUBLICATIONS

J. Wolfe, et al., "As Improved Catalyst System for Aromatic Carbon-Nitrogen Bond Formation: The Possible Involvement of Bis(Phosphine) Palladium Complexes as Key Intermediates", J. Am. Chem. Soc., 1996, 118, pp. 7215-7216.

S. Hauck, et al., "Tetraazacyclophanes by Palladium-Catalyzed Aromatic Amination. Geometrically Defined, Stable, High-Spin Diradicals", Organic Letters, vol. 1, No. 13, 1999, pp. 2057-2060.

J. Louie, et al., "Discrete High Molecular Weight Triarylamine Dendrimers Prepared by Palladium-Catalyzed Amination", J. Am. Chem. Soc., 1997, 119, pp. 11695-11696.

J. Wolfe, et al., "Palladium-Catalyzed Amination of Aryl Lodides", J. Org. Chem., 1996, 61, pp. 1133-1135.

T. Greene, et al., "Protection Groups in Organic Synthesis", 3$^{rd}$ Ed., John Wiley & Ons, Inc., pp. 579-580.

* cited by examiner

*Primary Examiner*—Thurman K. Page
*Assistant Examiner*—Chukwuma Nwaonicha
(74) *Attorney, Agent, or Firm*—Oblon, Spivak, McClelland, Maier & Neustadt, P.C.

(57) ABSTRACT

A method for producing aromatic amino compound (V):

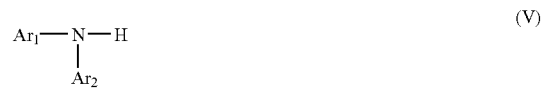

by synthesizing intermediate compound (IV):

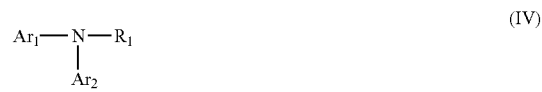

by the reaction of compound (I): $H_2N-R_1$ with a mixture of halogenated aryl compounds (II): $Ar_1-X$ and (III): $Ar_2-X$ in the presence of a noble metal catalyst, followed by eliminating the substituent $R_1$ from the nitrogen atom in compound (IV) under an acidic condition or an alkaline condition or by addition of a reducing agent or an oxidizing agent. ($R_1$: a substituent having 2 to 50 carbon atoms; $Ar_1$ and $Ar_2$: a substituted or unsubstituted hydrocarbon group or heterocyclic group having 6 to 50 carbon atoms and the same with or different from each other; and X: a halogen group). The aromatic amino compound useful as the charge transporting material can be produced efficiently at a great yield without using highly toxic raw materials.

6 Claims, No Drawings

METHOD FOR PRODUCING AROMATIC AMINO COMPOUND

CONTINUATION DATA

This application is a Continuation of prior U.S. application Ser. No. 10/469,702, filed on Sep. 12, 2003, now abandoned, which is National Stage of PCT/JP02/02132, filed Mar. 7, 2002.

TECHNICAL FIELD

The present invention relates to a novel method for producing an aromatic amino compound. More particularly, the present invention relates to a method for producing an aromatic amino compound useful as the charge transporting material in the fields of the electronic photosensitive materials and the organic electroluminescence devices without using highly toxic raw materials.

BACKGROUND ART

Application of aromatic amino compounds to the electronics field as functional material has been studied and the aromatic amino compounds are widely used as the charge transporting material in the fields of the electronic photosensitive materials and the organic electroluminescence devices. As the method for synthesizing the aromatic amino compounds, the Ullmann reaction is widely known. In accordance with the Ullmann reaction, an amino compound and an aromatic halogen compound are mixed together under stirring in the presence of a metal catalyst at a high temperature. This reaction has a drawback in that the yield is small. For example, the Ullmann reaction using aromatic amines is disclosed in Japanese Patent Application Laid-Open No. Heisei 8-48656 but the yield of the reaction is as small as 10 to 20%.

For synthesis of an aromatic amino compound, heretofore, the reaction routes using α-naphthylamine, β-naphthylamine, 4-aminodiphenyl or benzidine are known but these compounds exhibits strong toxicity. In particular, β-naphthylamine, 4-aminodiphenyl and benzidine are compounds listed as "Specified Chemical Substances" and the production of these compounds are prohibited.

DISCLOSURE OF THE INVENTION

The present invention has been made to overcome the above drawbacks and has an object of providing a method for producing an aromatic amino compound useful as the charge transporting material in the fields of the electronic photosensitive materials and the organic electroluminescence devices efficiently at a great yield without using highly toxic raw materials.

The present invention provides a process for producing an aromatic amino compound in accordance with any one of the following four reaction routes 1 to 4:

1. A method for producing an aromatic amino compound represented by following general formula (V):

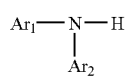

(V)

wherein $Ar_1$ and $Ar_2$ each independently represent a substituted or unsubstituted hydrocarbon group or heterocyclic group having 6 to 50 carbon atoms and may represent a same group or different groups, which comprises
synthesizing an intermediate compound for an aromatic amino compound which is represented by following general formula (IV):

(IV)

wherein $R_1$ represents a substituent having 2 to 50 carbon atoms, by reacting an amino compound represented by following general formula (I):

$$H_2N—R_1 \qquad (I)$$

wherein $R_1$ is as defined above, with a mixture of halogenated aryl compounds represented by following general formulae (II) and (III):

(II)

(III)

wherein $Ar_1$ and $Ar_2$ are as defines above, and X represents a halogen group, in a presence of a noble metal catalyst; and
eliminating the substituent represented by $R_1$ from the nitrogen atom in the compound represented by general formula (IV) either under an acidic condition or an alkaline condition or by addition of a reducing agent or an oxidizing agent.

2. A method for producing an aromatic amino compound represented by following general formula (VII):

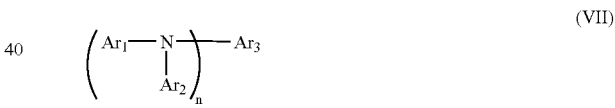

(VII)

wherein $Ar_1$ and $Ar_2$ each independently represent a substituted or unsubstituted hydrocarbon group or heterocyclic group having 6 to 50 carbon atoms and may represent a same group or different groups, $Ar_3$ represents a substituted or unsubstituted aromatic residue group having 6 to 60 carbon atoms, and n represents an integer of 1 to 4, which comprises
reacting an intermediate compound for an aromatic amino compound which is represented by following general formula (V):

(IV)

wherein $Ar_1$ and $Ar_2$ are as defined above, and X represents a halogen group, with a mixture of halogenated aryl compounds represented by following general formula (VI):

$$Ar_3—(X)_n \qquad (VI)$$

wherein $Ar_3$, X and n are as defined above, in a presence of a noble metal catalyst.

3. A method for producing an aromatic amino compound represented by following general formula (X):

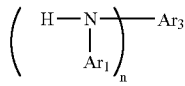 (X)

wherein $Ar_1$ represents a substituted or unsubstituted hydrocarbon group or heterocyclic group having 6 to 50 carbon atoms, $Ar_3$ represents a substituted or unsubstituted aromatic residue group having 6 to 60 carbon atoms, and n represents an integer of 1 to 4, which comprises synthesizing an intermediate compound of an aromatic amino compound represented by following general formula (VIII):

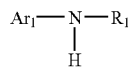 (VIII)

wherein $R_1$ represents a substituent having 2 to 50 carbon atoms, and $Ar_1$ is as defined above, by reacting an amino compound represented by following general formula (I):

 (I)

wherein $R_1$ is as defined above, with a halogenated aryl compound represented by following general formula (II):

 (II)

wherein $Ar_1$ is as defined above and X represents a halogen group, in a presence of a noble metal catalyst;

synthesizing another intermediate compound for an aromatic amino compound which is represented by following general formula (IX):

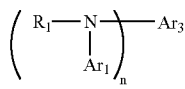 (IX)

wherein $R_1$, $Ar_1$, $Ar_3$ and n are as defined above, by reacting the compound represented by general formula (VIII) with a halogenated aryl compound represented by following general formula (VI):

 (VI)

wherein $Ar_3$, X and n are as defined above, in a presence of a noble metal catalyst; and eliminating the substituent represented by $R_1$ from the nitrogen atom in the compound represented by general formula (IX) either under an acidic condition or an alkaline condition or by addition of a reducing agent.

4. A method for producing an aromatic amino compound represented by general formula (VII):

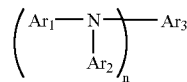 (VII)

wherein $Ar_1$ and $Ar_2$ each independently represent a substituted or unsubstituted hydrocarbon group or heterocyclic group having 6 to 50 carbon atoms and may represent a same group or different groups, $Ar_3$ represents a substituted or unsubstituted aromatic residue group having 6 to 60 carbon atoms, and n represents an integer of 1 to 4, which comprises reacting a compound represented by following general formula (X):

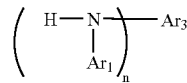 (X)

wherein $Ar_1$, $Ar_3$ and n are as defined above, with a halogenated aryl compound represented by following general formula (III):

 (III)

wherein $Ar_2$ is as defined above, and X represents a halogen group, in a presence of a noble metal catalyst.

THE MOST PREFERRED EMBODIMENT TO CARRY OUT THE INVENTION

The present invention will be described in detail in the following.

In the present invention, $R_1$ in the above formulae represents a substituent having 2 to 50 carbon atoms. As the substituent, for example, alkyl groups and arylalkyl groups are preferable and these groups having benzyl group or carbonyl group are more preferable. These groups may be substituted. Examples of the group having benzyl group include benzyl group, methoxybenzyl group and dimethoxybenzyl group. Examples of the group having carbonyl group include t-butoxycarbonyl group, benzyloxycarbonyl group, acetyl group, trifluoroacetyl group and benzoyl group. These groups are easily eliminated from the nitrogen atom by addition of an acid, an alkali, a reducing agent or an oxidizing agent. The above substituent is not particularly limited as long as the group has the above property.

In the present invention, $Ar_1$ and $Ar_2$ in the above formulae each independently represent a substituted or unsubstituted hydrocarbon group or heterocyclic group having 6 to 50 carbon atoms. Examples of the group represented by $Ar_1$ or $Ar_2$ include phenyl group, naphthyl group, anthranyl group, phenanthryl group, pyrenyl group, coronyl group, biphenyl group, terphenyl group, pyrrolyl group, furanyl group, thiophenyl group, benzothiophenyl group, oxadiazolyl group, indolyl group, carbazolyl group, pyridyl group, benzoquinolyl group, styrylphenyl group. Among these groups, biphenyl group, terphenyl group, 1-naphthyl group and 2-naphthyl group are preferable. These groups may be substituted.

In the present invention, $Ar_3$ in the above formulae represents a substituted or unsubstituted aromatic residue group having 6 to 60 carbon atoms. Examples of the group represented by $A_3$ include divalent groups such as phenylene group, naphthylene group, anthranylene group, phenanthrylene group, pyrenylene group, coronylene group, chrysenylene group, penylenylene group, bisanthracenylene group, biphenylene group, terphenylene group, pyrrolylene group, furanylene group, thiophenylene group, benzothiophenylene group, oxadiazolylene group, diphenylanthranylene group, indolylene group, carboxylylene group, pyridylene group, benzoquinolylene group, stilbene group, N,N,N-triarylamiono groups and N,N,N',N'-tetraaryldiamionoaryl groups. Among these groups, biphenylene group, terphenylene group, anthranylene group, tri-4-biphenylylamino group, N,N,N',N'-tetra(4-biphenylyl)benzidine group and stilbene group are preferable.

The above groups may be substituted or unsubstituted. Examples of the preferable substituent include alkyl groups having 1 to 6 carbon atoms such as ethyl group, methyl group, i-propyl group, n-propyl group, s-butyl group, t-butyl group, n-butyl group, pentyl group, hexyl group, cyclopentyl group and cyclohexyl group; alkoxyl groups having 1 to 6 carbon atoms such as ethoxyl group, methoxyl group, i-propoxyl group, n-propoxyl group, s-butoxyl group, t-butoxyl group, pentoxyl group, hexyloxy group, cyclopentoxyl group and cyclohexyloxyl group; and alkylamino groups having 1 to 8 carbon atoms such as dimethylamino group, diethylamino group, di-n-propylamino group, diisopropylainino group, di-n-butylamino group and piperidine group.

In the present invention, X in the above formulae represents a halogen atom. Examples of the halogen atom include chlorine atom, bromine atom and iodine atom. X may represent triflate group which works in a manner similar to that of halogen atoms.

In the present invention, a noble metal catalyst is used for forming the N—C bond. Examples of the noble metal catalyst include $Pd(OAc)_2$ (palladium acetate(II)), $Pd_2(dba)_3$ (tris(dibenzylideneacetone)-dipalladium(0), $Pd(dba)_2$ (bis(dibenzylideneacetone)palladium(0) and $Pd(dppf)Cl_2$ (1,1'-bis(diphenylphosphino)ferrocene)dichloropalladium (II). Examples of the ligand include $P(t-Bu)_3$ (tri-t-butylphosphine), BINAP ((2,2'-bis(diphenylphoshino)-1,1'-binaphthyl), $P(o-Tol)_3$ (tri-o-toluyl-phosphine), DPPF (1,1'-bis(diphenylphosphino)ferrocene) and DPPP (1,3-bis(diphenylphosphino)propane. Examples of the base include NaOtBu, $CsCO_3$, $K_2CO_3$ and NaOPh (sodium phenoxide). Examples of the solvent include toluene, xylene, mesitylene, THF and 1,4-dioxane. A suitable combination of these components is selected in accordance with the type of the substrate.

In the present invention, the N—C bond is broken and the substituent is eliminated from the nitrogen atom in an acidic or alkaline condition or by addition of a reducing agent. Examples of the acid used above include trifluoroacetic acid and hydrochloric acid. Examples of the base include KOH and NaOH. A solvent such as $CH_3OH$, $C_2H_5OH$ and water is suitably added.

Examples of the reducing agent include Pd, PdO and Pd/C and these compounds are used in combination with a compound supplying a hydride such as hydrogen gas, $HCO_2NH_4$ and silyl compounds. At least one solvent selected from methanol, ethanol, chloroform, acetic acid, ethyl acetate and dichloromethane is suitably used in accordance with the substrate although the solvent is not particularly limited. A reagent specifically interacting with the substrate may be used. For example, trimethylsilyl iodide may be used when benzyloxycarbonyl group which is a substituent represented by $R_1$ is eliminated.

Examples of the aromatic amino compound represented by general formula (V) which is produced in accordance with the method of the present invention include di-4-biphenylylamine, di-1,1':4',1''-terphenylyl-amine, di-1-naphthylamine, di-2-naphthylamine, (4-biphenylyl)-(2-napthyl-amine amine and (4-biphenylyl)(1,1':4',1''-terphenylyl)amine.

Examples of the aromatic amino compound represented by general formula (VII) which is produced in accordance with the method of the present invention include N,N,N',N'-tetra(4-biphenylyl)benzidine, N,N'-(2-naphthyl)(4-biphenylyl)benzidine, N,N'-(4-biphenylyl)(1,1':4',1''-terphenylyl)benzidine, N,N,N',N'-tetra(4-biphenylyl)-9,10-diamino-anthracene, N,N,N', N'-tetra(2-naphthyl)-6,12-diaminochrysene, N,N,N', N'-tetra(4-biphenylyl)-3,9-diaminoperylene, N,N,N',N',N'',N'''-hexa(4-biphenylyl)-1,3,5-triaminobenzene and N,N,N',N'-tetra-(2-naphthyl)-4,4'-diaminostilbene.

Examples of the aromatic amino compound represented by general formula (X) which is produced in accordance with the method of the present invention include N,N'-di(4-biphenylyl)benzidine, N,N'-di-(2-naphthyl)benzidine, N,N',N''-tri(4-biphenylyl)triaminobenzene, N,N'-di-(1,1':4',1''-terphenylyl)benzidine, N,N'-di(4-biphenylyl)-6,12-diamino-chrysene, N,N'-di(4-biphenylyl)-4,4''-diamino-p-terphenyl, N,N'-di-(2-naphthyl)-4,4'-diaminostilbene and N,N'-di(1-naphthyl)-4,4'-diamino-stilbene.

The present invention will be described more specifically with reference to examples in the following. However, the present invention is not limited to the examples.

EXAMPLE 1

Di-4-biphenylylamine and N,N,N',N'-tetra(4-biphenylyl) benzidine were prepared in accordance with the following reaction routes.

(1) N,N-Di(4-biphenylyl)benzylamine was prepared. The reaction scheme is shown in the following:

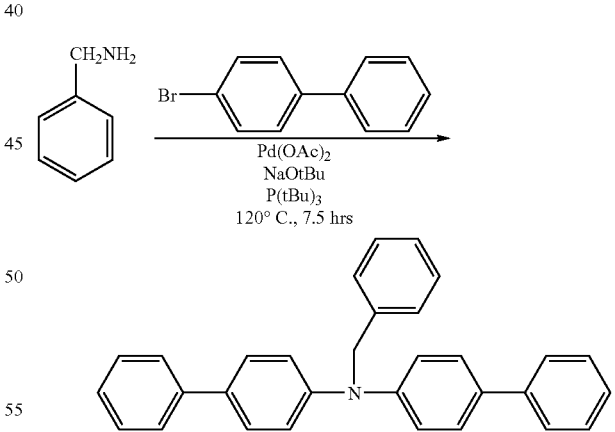

Into a 100 ml three-necked flask, 10.0 g (42.9 mmol, 2.3 eq) of 4-bromobiphenyl, 4.32 g (44.9 mmol, 2.4 eq) of sodium t-butoxide and 42.0 mg (0.187 mmol, 1.0% by mole) of palladium acetate were placed. A stirrer rod having the shape of a rugby ball was placed into the flask. A rubber cap was placed at each of two openings at the sides of the flask. A coiled tube condenser for refluxing was attached to the central opening of the flask and a three-way stopcock attached with a balloon containing the argon gas was attached to the top of the coiled tube condenser. The atmosphere in the system was purged with the argon gas in the balloon 3 times using a vacuum pump.

To the above system, 60 ml of dehydrated toluene, 2.04 ml (18.7 mmol) of benzylamine and 169 μl (0.374 mmol, 2.0% by mole) of a 2.22 moles/liter toluene solution of tris-t-butylphosphine were added using a syringe through a rubber septum and the resultant mixture was stirred at the room temperature for 5 minutes. Then, the flask was set into an oil bath and the temperature was raised slowly to 120° C. while the solution was stirred. After 7 and a half hours, the flask was removed from the oil bath to stop the reaction and left standing for one night under the atmosphere of argon.

The reaction mixture was transferred to a separation funnel. Dichloromethane in an amount of 300 ml was added and precipitates were dissolved. After washing with 60 ml of a saturated aqueous solution of sodium chloride, the organic layer was dried with anhydrous potassium carbonate. After potassium carbonate was removed by filtration, the organic solvent was removed by distillation from the organic layer. To the obtained residue, 200 ml of toluene and 40 ml of ethanol were added and the residue was completely dissolved by heating at 80° C. with attachment of a drying tube. The resultant solution was slowly cooled to the room temperature by being left standing for one night and the recrystallization was conducted. The formed crystals were separated by filtration using a Kiriyama funnel. After drying the crystals at 60° C. in vacuo, 6.73 g (16.4 mmol) of N,N-di(4-biphenylyl)benzylamine was obtained at a yield of 87%.

The results of the measurements of NMR and FD-MASS on the obtained N,N-di(4-biphenylyl)benzylamine were as follows:

NMR: $\delta_{90\ MHz}$ 5.07 (2H, s), 7.1 to 7.7 (23H, m) FD-MASS: 411

(2) Di-4-biphenylylamine was prepared. The reaction scheme is shown in the following:

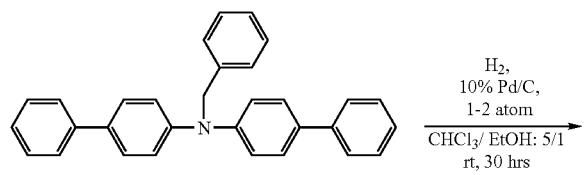

-continued

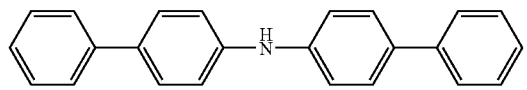

Into a 300 ml single-necked flask, 1.35 g (3.28 mmol) of N,N-di(4-biphenyl)benzylamine obtained in (1) and 135 mg (10% by weight) of palladium-active carbon (the content of palladium: 10% by weight) were placed. To the resultant mixture, 100 ml of chloroform and 20 ml of ethanol were added and the substrate was dissolved. A stirrer rod having the shape of a rugby ball was placed into the flask. A three-way stopcock attached with a balloon (a gas bag) containing 2 liters of the hydrogen gas was attached to the flask and the inside of the flask system was purged with the hydrogen gas 3 times using a vacuum pump. The hydrogen gas in the decreased amount was replenished and the volume of the hydrogen gas was adjusted at 2 liters. The resultant fluid was vigorously stirred at the room temperature. After the fluid was stirred for the total time of 30 hours at the room temperature, 100 ml of dichloromethane was added and the catalyst was removed by filtration. The obtained solution was transferred to a separation funnel and washed with 50 ml of a saturated solution of sodium hydrogencarbonate. The organic layer was separated, dried with anhydrous potassium carbonate and filtered and the solvent was removed by distillation. To the obtained residue, 50 ml of toluene was added and the recrystallization was conducted. The formed crystals were separated using a Kiriyama funnel and dried in vacuo at 50° C. and 990 mg (3.08 mmol) of di-4-biphenylylamine was obtained at a yield of 94%.

The results of the measurements of NMR and FD-MASS on the obtained di-4-biphenylylamine were as follows:

NMR: $\delta_{90\ MHz}$ 5.83 (1H, bs), 7.0 to 7.8 (18H, m) FD-MASS: 321

(3) N,N,N',N'-tetra(4-biphenylyl)benzidine was prepared. The reaction scheme is shown in the following:

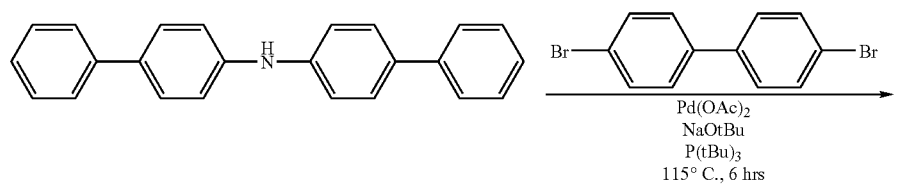

-continued

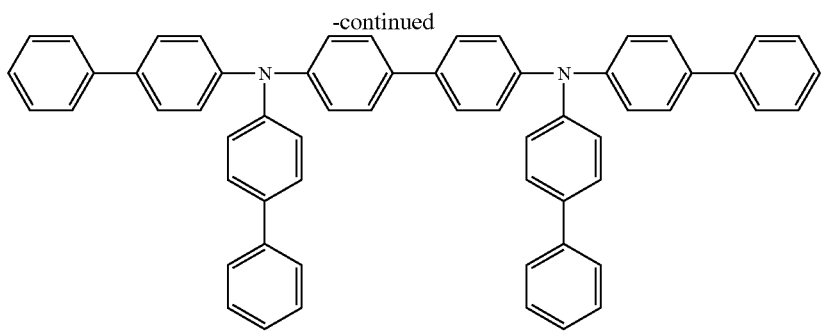

Into a 50 ml two-necked flask, 500 mg (1.56 mmol, 2.1 eq) of di-4-biphenylylamine obtained in (2), 231 mg (0.741 mmol) of 4,4'-dibromobiphenyl, 3.4 mg (0.0148 mmol, 2.0% by mole) of palladium acetate and 157 mg (1.63 mmol, 2.2 eq) of sodium t-butoxide were placed. A rubber cap was placed at the side opening of the flask. A coiled tube condenser for refluxing was attached to the central opening of the flask and a three-way stopcock attached with a balloon containing the argon gas was attached to the top of the coiled tube condenser. The atmosphere in the system was purged with the argon gas in the balloon 3 times using a vacuum pump.

To the above system, 10 ml of dehydrated toluene and 13.4 μl (0.0296 mmol, 4.0% by mole) of a 2.22 moles/liter toluene solution of tris-t-butylphosphine were added using a syringe through a rubber septum. Then, the flask was set into an oil bath and the temperature was raised slowly to 115° C. while the solution was stirred. After heating at 115° C. for 6 hours under stirring, the flask was removed from the oil bath and left standing at the room temperature for one night.

The formed precipitates were completely dissolved in 500 ml of dichloromethane. After the resultant solution was transferred to a separation funnel and washed with 100 ml of a saturated aqueous solution of sodium chloride, the organic layer (yellow) was dried with anhydrous potassium carbonate. After filtration, the organic solvent was removed by distillation and 150 ml of toluene and 50 ml of ethanol were added to the obtained residue. After a drying tube was attached, the precipitates were dissolved to some degree by heating at 80° C. and the resultant mixture was slowly cooled to the room temperature. The crystals in the system were separated by filtration using a Kiriyama funnel. After the crystals were washed with small amounts of toluene and ethanol and dried at 60° C. for 3 hours in a vacuum drying chamber, 453 mg (0.571 mmol) of N,N,N',N'-tetra(4-biphenylyl)benzidine was obtained at a yield of 77%.

The results of the measurements of NMR, FD-MASS and HPLC (high performance liquid chromatograph) on the obtained N,N,N',N'-tetra-(4-biphenylyl)benzidine were as follows:

NMR: $\delta_{90\ MHz}$ 7.1 to 7.8 (44H, m) FD-MASS: 792, 396 HPLC: The chemical purity: 99.5% or greater

EXAMPLE 2

N,N'-Di(4-biphenylyl)benzidine and N,N'-(2-naphthyl)-(4-biphenylyl)benzidine were prepared in accordance with the following reaction schemes.

(1) 4-Biphenylylbenzylamine was prepared. The reaction scheme is shown in the following:

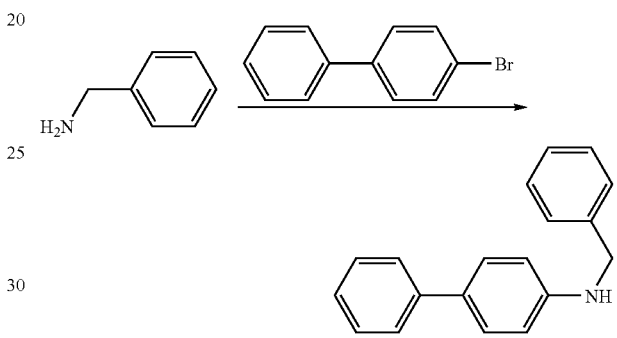

Into a 100 ml three-necked flask, 5.0 g (21.5 mmol, 1.15 eq) of 4-bromobiphenyl, 2.16 g (22.5 mmol, 1.2 eq) of sodium t-butoxide, 342 mg (0.374 mmol, 2.0% by mole) of $Pd_2(dba)_3$ and 467 mg (0.748 mmol, 4.0% by mole) of (s)-BINAP were placed. A stirrer rod having the shape of a rugby ball was placed into the flask. A rubber cap was placed at each of two openings at the sides of the flask. A coiled tube condenser for refluxing was attached to the central opening of the flask and a three-way stopcock attached with a balloon containing the argon gas was attached to the top of the coiled tube condenser. The atmosphere in the system was purged with the argon gas in the balloon 3 times using a vacuum pump.

To the above system, 60 ml of dehydrated toluene and 2.04 ml (18.7 mmol) of benzylamine were added using a syringe through a rubber septum and the resultant mixture was stirred at the room temperature for 5 minutes. Then, the flask was set into an oil bath and the temperature was raised slowly to 120° C. while the solution was stirred. After 6 hours, the flask was removed from the oil bath to stop the reaction and left standing for one night under the atmosphere of argon.

The reaction mixture was transferred to a separation funnel. Dichloromethane in an amount of 200 ml was added and precipitates were dissolved. After washing with 50 ml of a saturated aqueous solution of sodium chloride, the organic layer was dried with anhydrous potassium carbonate. After potassium carbonate was removed by filtration, the organic solvent was removed by distillation from an organic layer. The obtained product was separated and purified in accordance with the silica gel column chromatography and 3.82 g (16.4 mmol) of 4-biphenylyl-benzylamine was obtained at a yield of 79%.

The results of the measurements of NMR and FD-MASS on the obtained 4-biphenylylbenzylamine were as follows:

NMR: $\delta_{90\,MHz}$ 5.07 (2H, s), 5.78 (1H, bs), 7.1 to 7.7 (14H, m) FD-MASS: 259

(2) N,N-Dibenzyl-N',N'-di-4-biphenylylbenzidine was prepared. The reaction scheme is shown in the following:

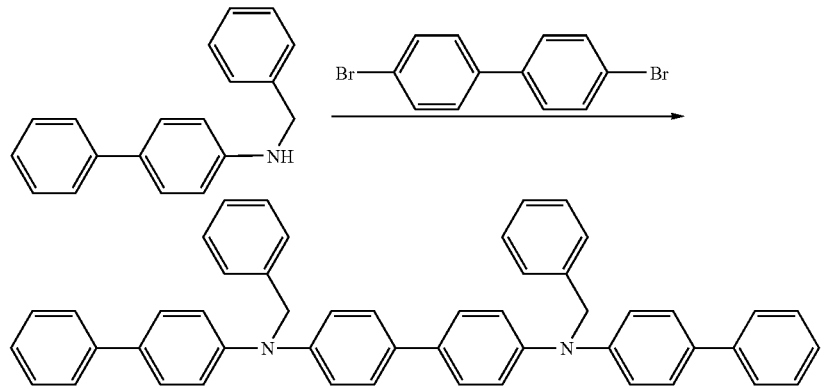

Into a 100 ml two-necked flask, 3.5 g (13.5 mmol, 2.1 eq) of 4-biphenylybenzylamine obtained in (1), 2.0 g mg (6.43 mmol) of 4,4'-dibromobiphenyl, 30 mg (0.128 mmol, 2.0% by mole) of palladium acetate and 1.36 g (14.8 mmol, 2.2 eq) of sodium t-butoxide were placed. A rubber cap was placed at the side opening of the flask. A coiled tube condenser for refluxing was attached to the central opening of the flask and a three-way stopcock attached with a balloon containing the argon gas was attached to the top of the coiled tube condenser. The atmosphere in the system was purged with the argon gas in the balloon 3 times using a vacuum pump.

To the above system, 60 ml of dehydrated toluene and 116 μl (0.256 mmol, 4.0% by mole) of a 2.22 moles/liter toluene solution of tris-t-butylphosphine were added using a syringe through a rubber septum. Then, the flask was set into an oil bath and the temperature was raised slowly to 115° C. while the solution was stirred. After heating for 6 hours under stirring, the flask was removed from the oil bath and left standing for one night.

The formed precipitates were completely dissolved in 300 ml of dichloromethane. After the resultant solution was transferred to a separation funnel and washed with 100 ml of a saturated aqueous solution of sodium chloride, the organic layer was dried with anhydrous potassium carbonate. After filtration, the organic solvent was removed by distillation. The product was recrystallized from a mixed solvent containing toluene and ethanol, separated by filtration and dried at 60° C. for 3 hours in a vacuum drying chamber and 3.80 g (5.69 mmol) of N,N-dibenzyl-N',N'-di-4-biphenylylbenzidine was obtained at a yield of 88%.

The results of the measurements of NMR and FD-MASS on the obtained N,N-dibenzyl-N',N'-di-4-biphenylylbenzidine were as follows:

NMR: $\delta_{90\,MHz}$ 5.08 (4H, s), 7.0 to 7.9 (36H, m) FD-MASS: 668

(3) N,N'-Di-(4-biphenylyl)benzidine was prepared. The reaction scheme is shown in the following:

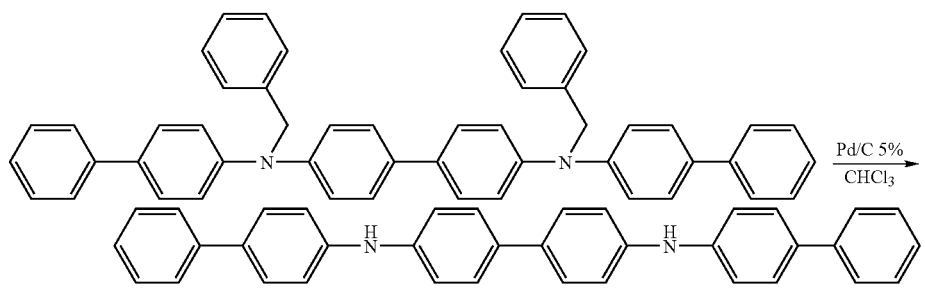

Into a 500 ml single-necked egg plant-shaped flask, 3.5 g (5.24 mmol) of N,N-dibenzyl-N',N'-di-4-biphenylylbenzidine obtained in (2) and 350 mg (10% by mole) of palladium-active carbon (the content of palladium: 5% by weight) were placed. To the resultant mixture, 350 ml of chloroform was added and the substrate was dissolved. A stirrer rod having the shape of a rugby ball was placed into the flask. A three-way stopcock attached with a balloon (a gas bag) containing 2 liters of the hydrogen gas was attached to the flask and the inside of the flask system was purged with the hydrogen gas 10 times using a vacuum pump. The hydrogen gas in the decreased amount was replenished and the volume of the hydrogen gas was adjusted at 2 liters. The resultant fluid was vigorously stirred at 35° C. After the fluid was stirred for the total time of 24 hours, the catalyst was removed by filtration. The obtained solution was transferred to a separation funnel and washed with 50 ml of a saturated solution of sodium hydrogencarbonate. The organic layer was separated, dried with anhydrous potassium carbonate and filtered and the solvent was removed by distillation. To the obtained residue, toluene was added and the recrystallization was conducted. The formed crystals were separated using a Kiriyama funnel and dried in vacuo at 50° C. and 2.33 g (4.77 mmol) of N,N'-di-(4-biphenylyl)benzidine was obtained at a yield of 91%.

The results of the measurements of NMR and FD-MASS on the obtained N,N'-di-(4-biphenylyl)benzidine were as follows:

NMR: $\delta_{90\ MHz}$ 5.80 (2H, bs), 7.0 to 7.8 (26H, m) FD-MASS: 488

(4) N,N'-(2-Naphthyl)(4-biphenylyl)benzidine was prepared. The reaction scheme is shown in the following:

To the above system, 50 ml of dehydrated toluene was added using a syringe through a rubber septum and the resultant mixture was stirred at the room temperature for 3 minutes. Then, the flask was set into an oil bath and the temperature was raised slowly to 120° C. while the solution was stirred. After 7 hours, the flask was removed from the oil bath to stop the reaction and left standing for one night under the atmosphere of argon.

The reaction mixture was filtered. The residue was washed with toluene, water and ethanol and recrystallized from xylene and 2.55 g (3.45 mmol) of N,N'-(2-naphthyl)(4-biphenylyl)benzidine was obtained at a yield of 84%.

The results of the measurements of NMR, FD-MASS and HPLC on the obtained N,N'-(2-naphthyl)(4-biphenylyl)benzidine were as follows:

NMR: $\delta_{90\ MHz}$ 7.0 to 7.9 (40H, m) FD-MASS: 740, 370 HPLC: The chemical purity: 99.8% or greater

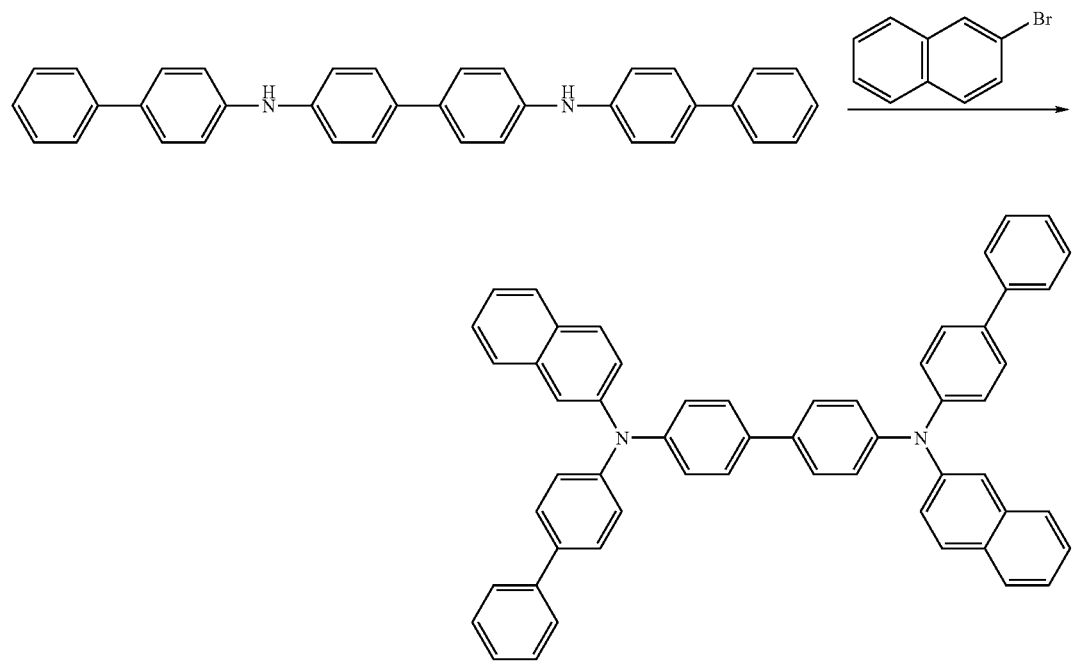

Into a 100 ml three-necked flask, 2.0 g (4.10 mmol) of N,N'-di(4-biphenylyl)benzidine obtained in (3), 1.87 g (9.02 mmol, 2.2 eq) of 2-bromonaphthalene, 945 mg (9.84 mmol, 2.4 eq) of sodium t-butoxide, 75 mg (0.082 mmol, 2.0% by mole) of Pd$_2$(dba)$_3$ and 103 mg (0.164 mmol, 4.0% by mole) of (s)-BINAP were placed. A stirrer rod having the shape of a rugby ball was placed into the flask. A rubber cap was placed at each of two openings at the sides of the flask. A coiled tube condenser for refluxing was attached to the central opening of the flask and a three-way stopcock attached with a balloon containing the argon gas was attached to the top of the coiled tube condenser. The atmosphere in the system was purged with the argon gas in the balloon 3 times using a vacuum pump.

EXAMPLE 3

N,N,N',N'-Tetra(2-naphthyl)-4,4'-diaminostilbene was prepared in accordance with the following reaction routes.
(1) N,N-Di(2-naphthyl)benzylamine was prepared. The reaction scheme is shown in the following:

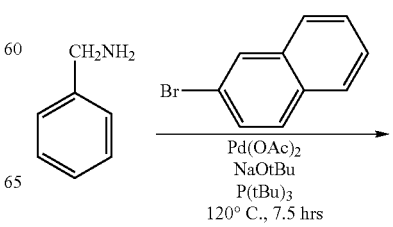

-continued

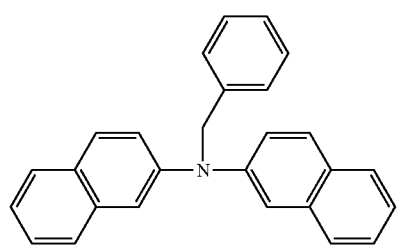

Into a 100 ml three-necked flask, 8.9 g (42.9 mmol, 2.3 eq) of 2-bromonaphthalene, 4.32 g (44.9 mmol, 2.4 eq) sodium t-butoxide and 42.0 mg (0.187 mmol, 1.0% by mole) of palladium acetate were placed. A stirrer rod having the shape of a rugby ball was placed into the flask. A rubber cap was placed at each of two openings at the sides of the flask. A coiled tube condenser for refluxing was attached to the central opening of the flask and a three-way stopcock attached with a balloon containing the argon gas was attached to the top of the coiled tube condenser. The atmosphere in the system was purged with the argon gas in the balloon 3 times using a vacuum pump.

To the above system, 60 ml of dehydrated toluene, 2.04 ml (18.7 mmol) of benzylamine and 169 µl (0.374 mmol, 2.0% by mole) of a 2.22 moles/liter toluene solution of tris-t-butylphosphine were added using a syringe through a rubber septum and the resultant mixture was stirred at the room temperature for 5 minutes. Then, the flask was set into an oil bath and the temperature was raised slowly while the solution was stirred. Formation of bubbles was observed when the temperature was about 80° C. and it was confirmed that the reaction was proceeding. The temperature was raised to 120° C. while the stirring was continued. The reaction system slowly changed to yellow and then to brown with the formation of white precipitates after 3 hours. Seven and a half hours after the temperature reached 120° C., the flask was removed from the oil bath to stop the reaction and left standing for one night under the atmosphere of argon.

The reaction mixture was transferred to a separation funnel. Dichloromethane in an amount of 300 ml was added and precipitates were dissolved. After washing with 60 ml of a saturated aqueous solution of sodium chloride, the organic layer was dried with anhydrous potassium carbonate. After potassium carbonate was removed by filtration with a filter paper and the filtrate was placed into a 500 ml egg-plant shaped flask, the organic solvent was removed by distillation from an organic layer. To the obtained residue, 200 ml of toluene and 40 ml of ethanol were added and the residue was completely dissolved by heating at 80° C. with attachment of a drying tube. The resultant solution was slowly cooled to the room temperature by being left standing for one night and the recrystallization was conducted. The formed crystals were separated by filtration using a Kiriyama funnel. After drying the crystals at 60° C. in vacuo, 3.94 g of white needle crystals having the shape of cotton were obtained. Using the filtrate, the crystallization was repeated and 1.48 g of the second product and 0.15 g of the third product were obtained. N,N-Di(2-naphthyl)benzylamine was obtained in a total amount of 5.57 g (15.5 mmol) at a yield of 83%.

The result of the measurements of FD-MASS on the obtained N-di(2-naphthyl)benzylamine was as follows:
FD-MASS: 359

(2) Di-2-naphthylamine was prepared. The reaction scheme is shown in the following:

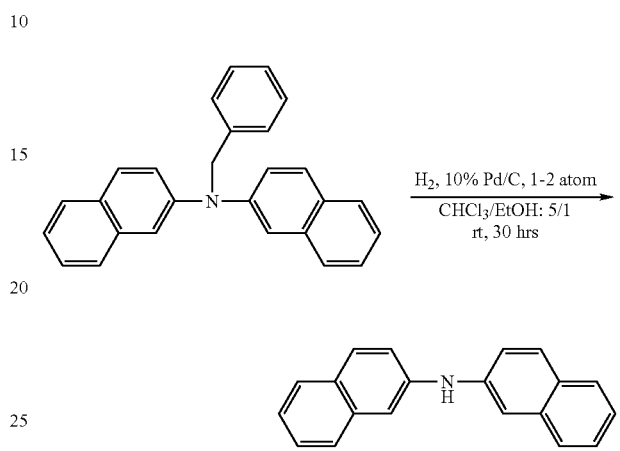

Into a 300 ml single-necked flask, 1.18 g (3.28 mmol) of N,N-di(2-naphthyl)benzylamine obtained in (1) and 135 mg (10% by weight) of palladium-active carbon (the content of palladium: 10% by weight) were placed. To the resultant mixture, 100 ml of chloroform and 20 ml of ethanol were added and the substrate was dissolved. A stirrer rod having the shape of a rugby ball was placed into the flask. A three-way stopcock attached with a balloon (a gas bag) containing 2 liters of the hydrogen gas was attached to the flask and the inside of the flask system was purged with the hydrogen gas 10 times using a vacuum pump. The hydrogen gas in the decreased amount was replenished and the volume of the hydrogen gas was adjusted at 2 liters. The resultant fluid was vigorously stirred at the room temperature. After the fluid was stirred for the total time of 30 hours at the room temperature, 100 ml of dichloromethane was added and the catalyst was removed by filtration. The obtained solution was transferred to a separation funnel and washed with 50 ml of a saturated solution of sodium hydrogencarbonate. The organic layer was separated, dried with anhydrous potassium carbonate and filtered and the solvent was removed by distillation. To the obtained residue, 50 ml of toluene was added. A drying tube was attached to the flask and the temperature was raised to 85° C. to dissolve the residue. The recrystallization was conducted by slowly cooling the resultant solution to the room temperature while the flask was left standing for one night. The formed crystals were separated using a Kiriyama funnel and dried in vacuo at 50° C. and 710 mg (2.62 mmol) of di-2-naphthylamine was obtained at a yield of 80%.

The result of the measurements of FD-MASS on the obtained di-2-naphthylamine was as follows:
FD-MASS: 269

(3) N,N,N',N'-tetra(2-naphthyl)-4,4'-diaminostilbene was prepared. The reaction scheme is shown in the following:

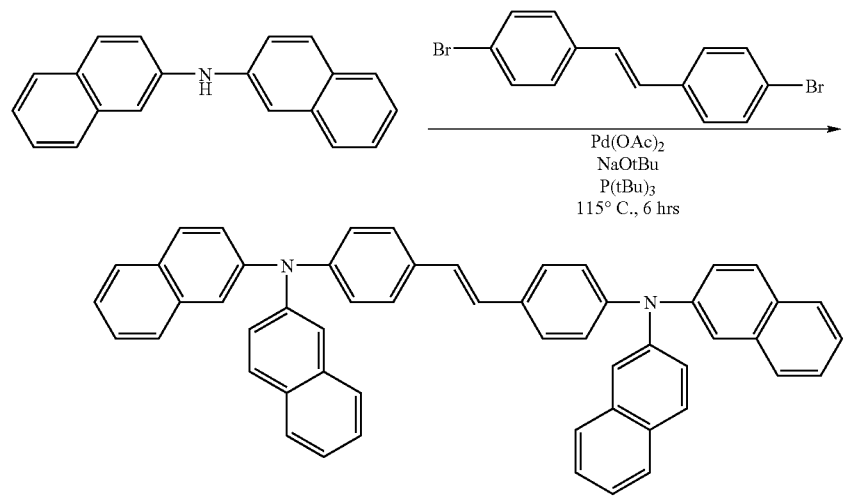

Into a 50 ml two-necked flask, 420 mg (1.56 mmol, 2.1 eq) of di-2-naphthylamine obtained in (2), 250 mg (0.741 mmol) of 4,4'-dibromostilbene, 3.4 mg (0.0148 mmol, 2.0% by mole) of palladium acetate and 157 mg (1.63 mmol, 2.2 eq) of sodium t-butoxide were placed. A rubber cap was placed at the side opening of the flask. A coiled tube condenser for refluxing was attached to the central opening of the flask and a three-way stopcock attached with a balloon containing the argon gas was attached to the top of the coiled tube condenser. The atmosphere in the system was purged with the argon gas in the balloon 3 times using a vacuum pump.

To the above system, 10 ml of dehydrated toluene and 13.4 μl (0.0296 mmol, 4.0% by mole) of a 2.22 moles/liter toluene solution of tris-t-butylphosphine were added using a syringe through a rubber septum. Then, the flask was set into an oil bath and the temperature was, raised slowly to 115° C. while the solution was stirred. Brownish white precipitates were formed in the reaction solution after 30 minutes. After heating at 115° C. for 6 hours under stirring, the flask was removed from the oil bath and left standing for one night.

The formed precipitates were completely dissolved in 500 ml of dichloromethane. After the resultant fluid was transferred to a separation funnel and washed with 100 ml of a saturated aqueous solution of sodium chloride, the organic layer (yellow) was dried with anhydrous potassium carbonate. After filtration, the organic solvent was removed by distillation and 150 ml of toluene and 50 ml of ethanol were added to the obtained residue. After a drying tube was attached to the flask, the precipitates were dissolved to some degree by heating at 80° C. and the resultant mixture was slowly cooled to the room temperature. The crystals of the ivory color in the system were separated by filtration using a Kiriyama funnel. After the crystals were washed with small amounts of toluene and ethanol and dried at 60° C. for 3 hours in a vacuum drying chamber, 428 mg (0.600 mmol) of N,N,N',N'-tetra(2-naphthyl)-4,4'-diaminostilbene was obtained at a yield of 81%.

The results of the measurements of NMR and FD-MASS on the obtained N,N,N',N'-tetra(2-naphthyl)-4,4'-diaminostilbene were as follows:

NMR: $\delta_{90\ MHz}$ 6.9 to 7.9 (38H, m) FD-MASS: 714

COMPARATIVE EXAMPLE 1

N,N,N',N'-Tetra(4-biphenylyl)benzidine was prepared in accordance with a conventional method.

4-Aminobiphenyl in an amount of 72.5 g (0.429 moles), 120 g (0.429 moles) of 4-iodobiphenyl, 32.6 g (0.236 moles) of potassium carbonate, 6.8 g (0.107 moles) of copper and 430 ml of nitrobenzene were placed into a reactor and the reaction was allowed to proceed at 210° C. for one night. When the reaction was completed, the reaction mixture was cooled by being left standing. Copper salts were removed by filtration under a reduced pressure. The filtrate was washed with chloroform and the solvent in the filtrate was removed by distillation under a reduced pressure. To the resultant residue, 500 ml of methanol was added. The obtained mixture was cooled and the formed crystals were separated by filtration. The obtained crystals in an amount of 49 g were dissolved into 250 ml of dimethylformamide (DMF) by heating. The resultant solution was cooled with water and tribiphenylamine of a byproduct precipitated by the cooling was removed by filtration. The filtrate was added into 1,000 ml of water and the formed crystals were separated by filtration, washed with water and methanol. The obtained crystals in an amount of 35 g which contained water were recrystallized from 750 ml of toluene and yellowish green scale-like crystals of di(4-biphenyl)amine were obtained. The mother liquor was concentrated and secondary crystals were obtained. The amount of the obtained product was 19 g (the yield: 13.8%). Into a reactor, 15 g (0.0467 moles) of di(4-biphenyl)amine, 9.5 g (0.0234 moles) of 4,4'-diiodobiphenyl, 9.7 g (0.0702 moles) of potassium carbonate, 0.74 g (0.0117 moles) of copper and 76 ml of nitrobenzene were placed and the reaction was allowed to proceed at 220° C. for 2 days. When the reaction was completed, 750 ml of DMF was added and copper salts were removed by filtration while the temperature of the reaction mixture remained high. The filtrate was cooled and the formed crystals were separated by filtration. The obtained crystals in an amount of 25 g which contained water were recrystallized 3 times from toluene in an amount 100 time as much as that of the crystals and light yellow crystals of N,N,N',N'-tetra(4-biphenyl)benzidine as the object compound were obtained (the amount of the obtained product: 9 g; the yield: 48.6%).

INDUSTRIAL APPLICABILITY

As described in detail in the above, in accordance with the method of the present invention, the aromatic amino compounds useful as the charge transporting material in the fields of the electronic photosensitive materials and the organic electroluminescence devices can be produced efficiently at a great yield without using highly toxic raw materials.

The invention claimed is:

1. A method for producing an aromatic amino compound represented by general formula (V):

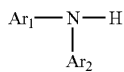 (V)

wherein $Ar_1$ and $Ar_2$ each independently represent a substituted or unsubstituted hydrocarbon group or heterocyclic group having 6 to 50 carbon atoms and may represent the same group or different groups, wherein the method comprises:

synthesizing an intermediate compound represented by general formula (IV):

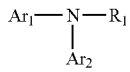 (IV)

wherein $R_1$ represents a substituent having 2 to 50 carbon atoms, by reacting an amino compound represented by general formula (I):

$H_2N\text{-}R_1$ (I)

wherein $R_1$ is as defined above, with a mixture of halogenated aryl compounds represented by general formulae (II) and (III):

$Ar_1$—X (II)

$Ar_2$—X (III)

wherein $Ar_1$ and $Ar_2$ are as defined above, and X represents a halogen group, in the presence of a noble metal catalyst; and eliminating the substituent represented by $R_1$ from the nitrogen atom in the compound represented by general formula (IV) either under an acidic condition or an alkaline condition or by addition of a reducing agent or an oxidizing agent.

2. The method according to claim 1, wherein the substituent represented by $R_1$ is a substituted or unsubstituted arylalkyl group.

3. The method according to claim 1, wherein the substituent represented by $R_1$ has carbonyl group.

4. The method according to claim 1, wherein $Ar_1$ and $Ar_2$ each independently represent a substituted or unsubstituted biphenyl group, a substituted or unsubstituted terphenyl group, a substituted or unsubstituted 1-naphthyl group or a substituted or unsubstituted 2-naphthyl group.

5. The method according to claim 1, wherein the aromatic amino compound is a charge transporting material.

6. The method according to claim 1, wherein the aromatic amino compound is a charge transporting material for organic electroluminescence devices.

* * * * *